United States Patent
Boroczky et al.

(10) Patent No.: US 11,004,196 B2
(45) Date of Patent: May 11, 2021

(54) ADVANCED COMPUTER-AIDED DIAGNOSIS OF LUNG NODULES

(71) Applicant: KONINKLIJKE PHILIPS N.V., Eindhoven (NL)

(72) Inventors: Lilla Boroczky, Mt. Kisco, NY (US); Lalitha Agnihotri, Tarrytown, NY (US); Luyin Zhao, Lawrenceville, NJ (US); Michael Chun-chieh Lee, Lexington, MA (US); Charles Andrew Powell, River Vale, NJ (US); Alain C. Borczuk, Roslyn Heights, NY (US); Steven Kawut, Florham Park, NJ (US)

(73) Assignee: Koninklijke Philips N.V., Eindhoven (NL)

(*) Notice: Subject to any disclaimer, the term of this patent is extended or adjusted under 35 U.S.C. 154(b) by 238 days.

(21) Appl. No.: 16/152,487

(22) Filed: Oct. 5, 2018

(65) Prior Publication Data

US 2019/0108632 A1 Apr. 11, 2019

Related U.S. Application Data

(62) Division of application No. 12/441,950, filed as application No. PCT/IB2007/053776 on Sep. 18, 2007, now Pat. No. 10,121,243.

(51) Int. Cl.
*G06T 7/00* (2017.01)
*G06T 7/48* (2017.01)
(Continued)

(52) U.S. Cl.
CPC .......... *G06T 7/0012* (2013.01); *A61B 6/5217* (2013.01); *A61B 6/5223* (2013.01);
(Continued)

(58) Field of Classification Search
None
See application file for complete search history.

(56) References Cited

U.S. PATENT DOCUMENTS 6,694,046 B2   2/2004   Doi et al.
6,748,044 B2   6/2004   Sabol et al.
(Continued)

FOREIGN PATENT DOCUMENTS

JP   2003275196 A   9/2003
JP   2004105729 A   4/2004
(Continued)

OTHER PUBLICATIONS

Gurcan et al., "Lung nodule detection on thoracic computed tomography images: Preliminary evaluation of a computer-aided diagnosis system"., Medical Physics, vol. 29, No. 1, pp. 2552-2558, Nov. 2002.
(Continued)

*Primary Examiner* — Samah A Beg

(57) ABSTRACT

Methods are herein provided for decision support in diagnosis of a disease in a subject, and for extracting features from a multi-slice data set. Systems for computer-aided diagnosis are provided. The systems take as input a plurality of medical data and produces as output a diagnosis based upon this data. The inputs may consist of a combination of image data and clinical data. Diagnosis is performed through feature selection and the use of one or more classifier algorithms.

18 Claims, 6 Drawing Sheets

(51) Int. Cl.
*A61B 6/00* (2006.01)
*G06F 19/00* (2018.01)

(52) U.S. Cl.
CPC .............. *G06F 19/00* (2013.01); *G06T 7/48* (2017.01); *G06T 2207/30061* (2013.01)

(56) References Cited

U.S. PATENT DOCUMENTS

| | | | |
|---|---|---|---|
| 6,898,303 | B2 | 5/2005 | Armato et al. |
| 7,058,210 | B2* | 6/2006 | Mundy ............... A61B 6/00 382/128 |
| 7,356,173 | B2 | 4/2008 | Wiemker |
| 7,374,077 | B2 | 5/2008 | Shimura |
| 7,379,572 | B2 | 5/2008 | Yoshida et al. |
| 7,640,051 | B2 | 12/2009 | Krishnan et al. |
| 10,524,823 | B2* | 1/2020 | Sakuragi ............. G06T 19/00 |
| 2001/0043729 | A1 | 11/2001 | Giger et al. |
| 2002/0172403 | A1* | 11/2002 | Doi ................. G06T 7/0012 382/128 |
| 2003/0174873 | A1 | 9/2003 | Giger et al. |
| 2004/0101104 | A1* | 5/2004 | Avinash ............. A61B 6/463 378/98.12 |
| 2004/0252870 | A1* | 12/2004 | Reeves ............. G06T 7/0012 382/128 |
| 2004/0267102 | A1* | 12/2004 | Skladnev ........... A61B 5/442 600/315 |
| 2005/0027188 | A1 | 2/2005 | Metaxas et al. |
| 2005/0105794 | A1 | 5/2005 | Fung |
| 2005/0207630 | A1* | 9/2005 | Chan .................. A61B 6/583 382/131 |
| 2005/0232474 | A1* | 10/2005 | Wei ..................... G06T 7/11 382/128 |
| 2006/0013460 | A1* | 1/2006 | Dehmeshki ......... G06T 7/0012 382/131 |
| 2006/0122865 | A1 | 6/2006 | Preiss et al. |
| 2006/0177125 | A1* | 8/2006 | Chan .................. G06T 7/44 382/154 |
| 2006/0235881 | A1 | 10/2006 | Masarie et al. |
| 2019/0333197 | A1* | 10/2019 | Kask .................. G06F 3/40 |
| 2020/0000362 | A1* | 1/2020 | Wallace ............. A61B 5/055 |

FOREIGN PATENT DOCUMENTS

| | | |
|---|---|---|
| JP | 2005278690 A | 10/2005 |
| WO | 2004088589 A1 | 10/2004 |
| WO | 2005001740 A2 | 1/2005 |
| WO | 2005001742 A2 | 1/2006 |
| WO | 2006054267 A1 | 5/2006 |
| WO | 2006054272 A2 | 5/2006 |

OTHER PUBLICATIONS

Campadelli et al., "Support Vector machines for candidate nodules classification", Neurocomputing, vol. 68, pp. 281-288, Mar. 31, 2005.

Awai et al., "Pulmonary Nodules: Estimation of Malignancy at thin-section helical CT effect of computer-aided diagnosis on performance of radiologists", Radiology, vol. 239, No. 1, pp. 276-284, 2006.

Mousa et al., "Lung Nodule classification utilizing support vector machines", IEEE ICIP 2002, pp. 153-156.

Kakeda et al., "Improved detection of lung nodules on chest radiographs using a commercial computer aided diagnosis system", American Journal of Radiology, vol. 182, Feb. 2004, pp. 505-510.

Suzuki et al., "Computer aided diagnostic scheme for distinction between benign and malignant nodules in thoracic low dose CT by use of massive etraining artificial neural network", IEEE Trans. on Medical Imaging, vol. 24, No. 9, pp. 1138-1150, 2005.

Way et al., "Computer-Aided Diagnosis of Pulmonary Nodules on CT Scans Segmentation and Classification using 3D Active Contours", ME Phys. 33(7), pp. 2323-2337, 2006.

Amadsun et al., "Textural Features Corresponding to Textural Properties", IEEE Trans. Sys Man and Cybernetics, vol. 19, No. 5, pp. 1264-1274, 1989.

Philips Press Release, "Philips New CT Lung Nodule Assessment and Comparison Option Can Enable Clinicians to Identify and Treat Lung Cancer", Mar. 7, 2003.

Wiemker et al., "Option to improve the performance of the computer aided detection of lung nodules in thin slice CT", Philips Research laboratories, Nov. 2003, pp. 1-19.

Nixon et al., "Feature Extraction & Image Processing", Butterworth-Heinemann: Woburn, MA, 2003, pp. 269-278.

Wiemker et al., "Computer Aided Tumor Volumetry in CT Data", Invention Disclosure, Philips Research Hamburg, 2002, Now Wo2004/088589A1.

* cited by examiner

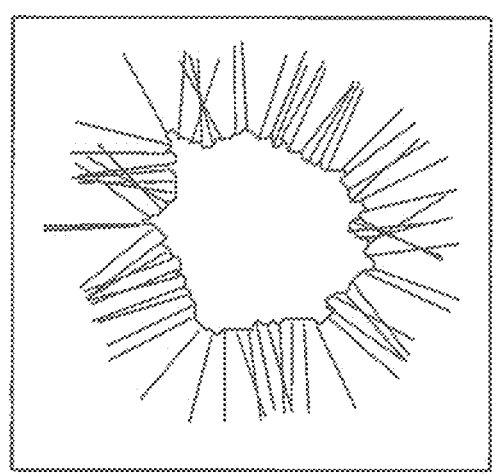
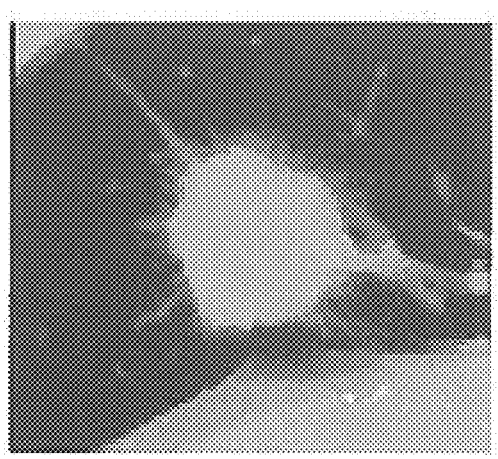
FIG. 3

ADVANCED COMPUTER-AIDED DIAGNOSIS OF LUNG NODULES

CROSS REFERENCE TO RELATED APPLICATIONS

This application is a divisional of prior application Ser. No. 12/441,950, filed Jul. 28, 2010, which is a national stage entry of PCT/IB2007/053776, filed Sep. 18, 2007, the content of which is incorporated herein by reference in its entirety.

Systems and methods are provided for advanced computer-aided diagnosis.

Lung cancer is a common and often fatal disease. Despite improvements in surgical techniques and therapies, the 5-year survival rate of lung cancer patients remains at only about 15%. However, the 5-year survival rate is about 50% for cases detected when the disease is still localized. Early detection and diagnosis of suspicious lesions allow early intervention and can lead to an improved prognosis.

Characterization of lung nodules is a major challenge, as even experts often disagree about which lung nodules are cancerous. Misdiagnosing malignant nodules causes delay in treatment. To minimize misdiagnosis, many patients undergo biopsies, which negatively impact the physical and psychological well-being of the patients as well as impose a large financial burden on patients and insurance providers.

Recent advances in multi-slice computed tomography (MSCT) make the detection and diagnosis of lung cancer possible at an earlier stage than ever before. However, such systems generate a large amount of data to be interpreted by radiologists. This in turn increases the importance of clinical decision support systems (CDSS). An example of CDSS is computer-aided detection (CAD) systems. CAD systems which automatically identify potential lesions in MSCT scans, such as lung nodules from thoracic MSCT scans, have already gained FDA approval and are available on the market. In contrast, computer-aided diagnosis (CADx) systems which characterize detected lesions remain in the research stage (Awai et al., Radiology, Vol. 239, No. 1, pp. 276-284, 2006; Suzuki et al., IEEE Trans. on Medical Imaging, Vol. 24, No. 9, pp. 1138-1150, 2005; and Way et al., Me. Phys., 33 (7), pp. 2323-2337, 2006).

CADx algorithms typically rely upon machine learning techniques to relate a set of input features to a desired diagnostic output. For example, in computed tomography (CT) imaging of the lung for lung cancer diagnosis, these input features may include the results of image processing algorithms as applied to the lung nodule under investigation. The process of identifying image features for use in machine learning is known as feature extraction. Improving the diagnostic accuracy of CADx systems is a key step to successful introduction of this technology into the clinic. One approach to improving the performance of CADx is to improve the feature extraction process.

CADx systems that characterize the detected lesions remain in the research stage, and even many recent systems described in the literature fail to incorporate clinical information, or to use optimized feature extraction, or to apply advanced machine learning techniques.

Accordingly, methods and systems of providing decision support in diagnosis of a disease in a subject are provided herein. The methods in one embodiment include extracting an image-based volume of interest in the subject; segmenting the image to delineate at least one lesion within the volume of interest from a background of the image; extracting image-based features in a plurality of dimensions; converting clinical information into a compatible format and combining the clinical information with the image-based features to form a feature pool; and selecting an optimal feature subset or an optimal group of feature subsets from the subset pool to be used by a classifier or committee of classifiers that outputs a decision, where the classifier or committee of classifiers provides a prediction of diagnosis of the lesion.

A related embodiment further includes interpolating between slices of the volume of interest to create an isotropic or near-isotropic voxel representation.

In any of these embodiments, the plurality of dimensions includes 2 dimensions, 2.5 dimensions, and 3 dimensions for image-based feature extraction.

A related embodiment further includes an optimal feature subset including at least one of a genetic algorithm, a statistical difference filter, a correlation filter, a recursive feature elimination, a stepwise linear regression, and a random feature selection.

In a related embodiment, clinical information is converted into multiple clinical feature categories.

In another related embodiment, the classifier or committee of classifiers is a support vector machine, a decision tree, linear discriminant analysis, or a neural network.

In yet another embodiment, the classifier or committee of classifiers determines whether the at least one lesion is malignant or benign. In a related embodiment, the classifier or committee of classifiers determine a likelihood of malignancy of the at least one lesion. The determination by the classifier or committee of classifiers is determined by at least one calculation such as a simple mean value, a simple vote, a weighted mean value, or a weighted vote.

Systems for computer-aided diagnosis are provided that include a pre-processing unit to extract an image-based region of interest; an interpolation unit to create isotropic or near-isotropic voxel representation; a segmentation unit to delineate at least one lesion in the region of interest; a feature extraction unit to extract image-based features in a plurality of dimensions from the image of the region of interest; a clinical information processing unit to accept and convert clinical information into a compatible format; and a classifier or committee of classifiers that uses the image-based features and the clinical information to output a decision.

A related embodiment further includes a feature selection unit to select, during training of the system, relevant image-based features and clinical features from a feature pool. In another related embodiment, the feature selection unit further includes an optimization technique such as a genetic algorithm, a statistical difference filter, a correlation filter, a recursive feature elimination, a stepwise linear regression and a random feature selection; and a classifier or committee of classifiers selected that include a support vector machine, a decision tree, linear discriminant analysis, and a neural network.

In a related embodiment, the image-based region of interest is constructed by performing at least one morphological operation. The at least one morphological operation includes erosion, dilation, and hole-filling.

A related embodiment further includes the image-based region of interest constructed by selecting the largest contiguous object resulting from the segmentation. In another related embodiment, the image-based region of interest includes an internal region, an external region, and a boundary region, where unwanted elements are excluded from the region of interest.

In another related embodiment, the clinical information further includes at least one data point selected from age, gender, smoking history, cancer history, family history, occupational exposure, recreational exposure, past pulmonary diseases, present pulmonary diseases, prior chest surgery, number of satellite lesions around the lesion to be diagnosed, size of lymph nodes, presence of suspicious nodes, and location of the lesion in the lung.

In a related embodiment, the classifier determines if a lesion is malignant or benign. In another related embodiment, the classifier determines a likelihood of malignancy of a lesion.

In yet another embodiment, a method of extracting features from a multi-slice data set is provided, where the method includes steps of representing a spatial distribution of an object mathematically; representing a shape of the object mathematically; determining contour and texture of the object; identifying a border pixel of a lesion and estimating a derivative; analyzing the derivative as a function of position along the contour; identifying automatically the presence of dark regions or bright regions within the object; and approximating texture of an image in a surrounding region of the object.

A related embodiment further includes selecting an individual slice from the multi-slice data set for analysis by a manual selection by a user or by an automatic selection of a largest slice.

In a related embodiment, features are calculated for at least one of: each slice of the multi-slice data set; a maximum intensity projection taken at an arbitrary angle, a minimum intensity projection taken at an arbitrary angle, and a digitally reconstructed radiograph taken at an arbitrary angle through one or more slices of the image. In another related embodiment, the features calculated for each slice of the multi-slice data set are combined by a method including calculating a weighted average in which weights are proportional to a number of pixels on each slice; finding a maximum value across multiple slices of the multi-slice dataset; and finding a minimum value across the multiple slices of the multi-slice data set. In another related embodiment, the features are calculated in each of a plurality of dimensions.

In another embodiment, the shape of the object is described by at least one of distribution of coefficients after a Fourier transform of border pixel positions; mathematical moments of a segmented object that are invariant to translation, rotation, and scaling; mathematical moments of a grayscale distribution of image pixels; fractal dimension; and a chain code.

In another embodiment, the texture of the object is described by at least one of fractal dimension; energy, entropy, maximum probability, inertia, inverse difference and correlation based on a gray-level co-occurrence matrix; and coarseness, contrast, busyness, complexity and strength based on a neighborhood gray-tone difference matrix. In yet another embodiment, the surrounding region is described by at least one of a derivative of image intensity along a direction orthogonal to a local contour; a derivative of the image intensity along the direction orthogonal to the local contour and moments of a power spectrum; and an estimate of variance of the image intensity along the direction orthogonal to the local contour.

In yet another embodiment, the presence of dark regions and bright regions within the object is described by the intensity or size of clusters of contiguous pixels above or below a given threshold.

Methods and systems are provided herein in order to pre-process medical images and provide features that are used as inputs into a CADx system. Advanced image processing and machine learning techniques are applied and clinical information about patients is integrated to provide decision support in diagnosis. The methods and systems provided herein achieve high specificity and sensitivity, and characterize lesions in a plurality of dimensions to more accurately distinguish benign lesions from malignant lesions.

The methods and systems provided herein can either give a binary decision, i.e. whether a nodule is malignant or benign, or can provide a probability or a likelihood (e.g. 80%) that a nodule or lesion is malignant. Clinicians use this information as a second opinion to assist in their diagnostic decision making. The methods and systems provided herein can be used for different diseases (e.g. a colon polyp, liver cancer, or breast cancer) and different modalities, such as MRI or CT.

FIG. 3, Panel A is a scan of a nodule.

FIG. 3, Panel B is a corresponding segmented contour drawing and the estimated normal angles.

Figure 4:
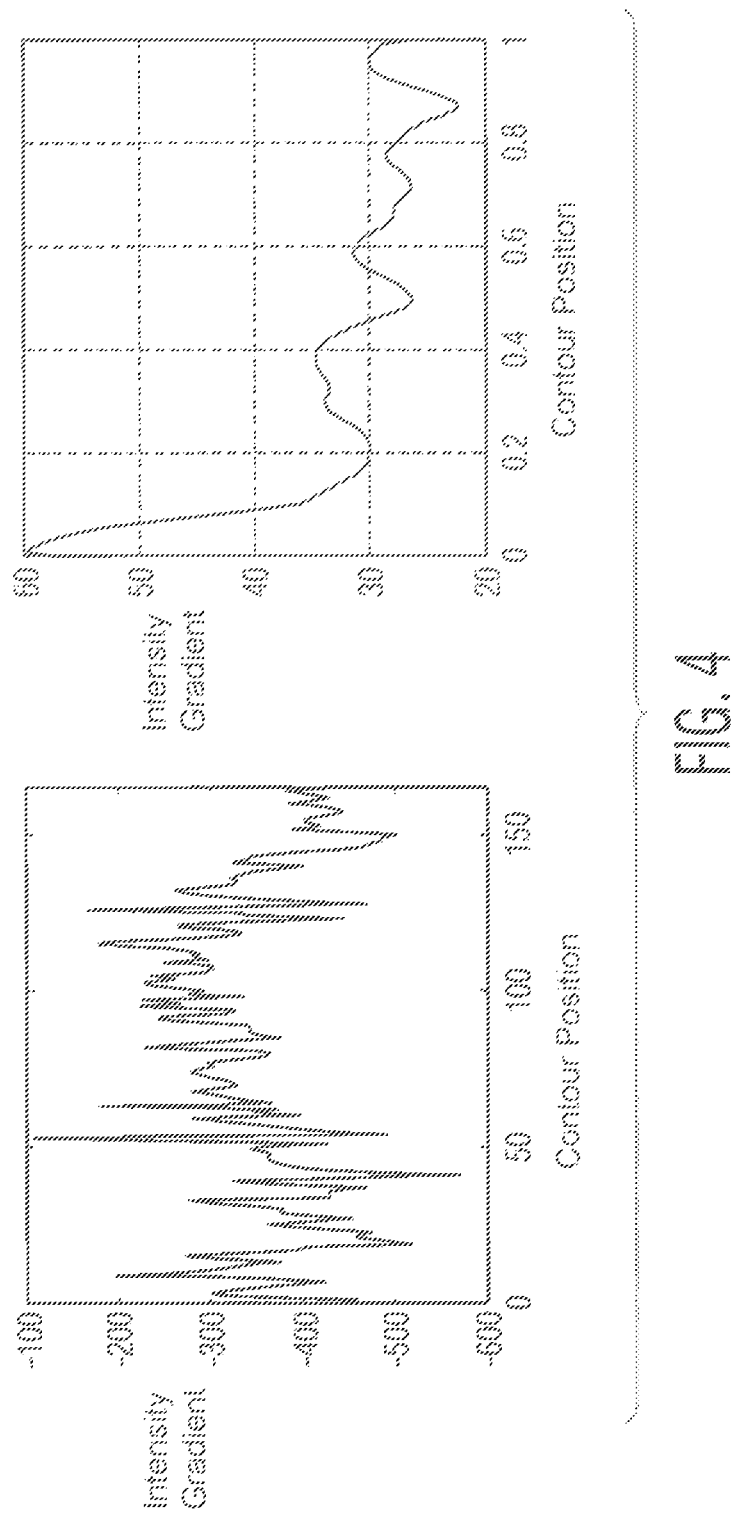

FIG. 4, Panel A is a graph of the intensity gradient of a nodule, with gradient on the ordinate and position along contour on the abscissa.

FIG. 4, Panel B is a graph of the corresponding power spectrum, with power/frequency on the ordinate and normalized frequency on the abscissa.

Figure 5:
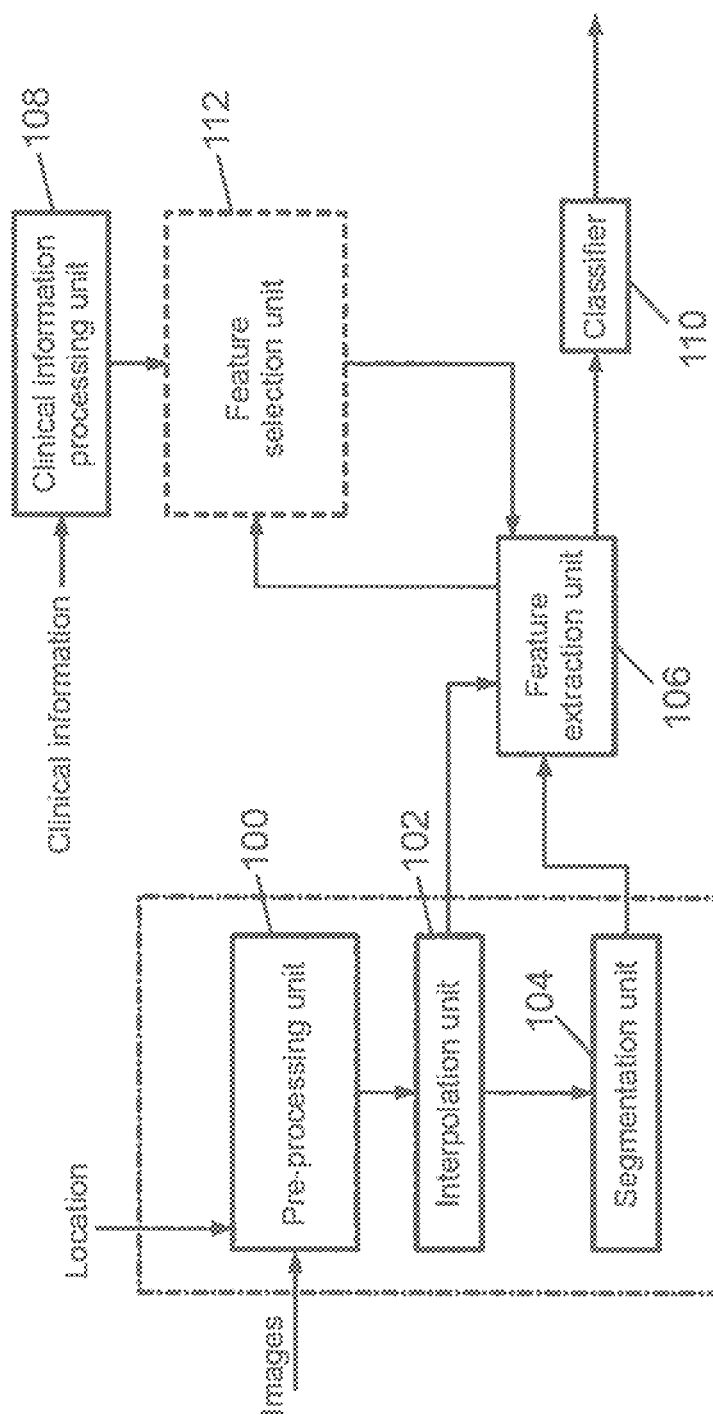

FIG. 5 is a block diagram of a CADx system.

Figure 6:
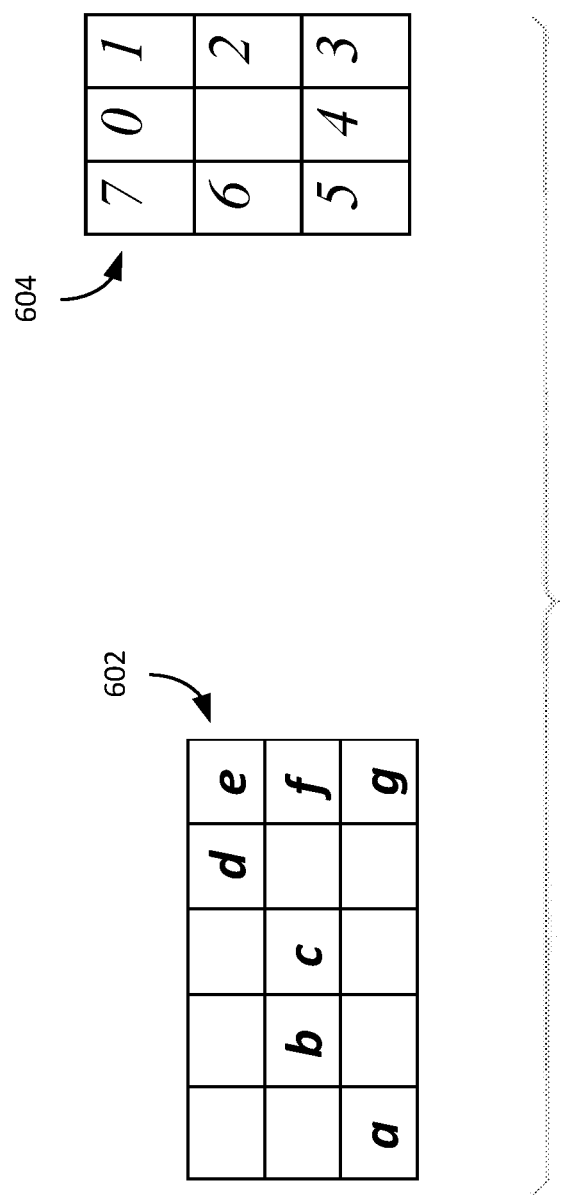

FIG. 6 depicts an example image with internal boundary and a chain code encoder template.

A CADx system that provides high confidence to clinicians improves clinician workflow by providing fast and accurate diagnosis (fewer false positives and false negatives). A CADx system can be used as a second reader to increase clinicians' confidence in their diagnosis, leading to significant reduction of unnecessary biopsies of lung lesions such as nodules. Furthermore, a CADx system can facilitate lung cancer screening of asymptomatic patients since diagnosis can be reached quickly and accurately. MSCT scanners, exemplified but not limited to the Philips Brilliance series, offer increasing resolution and allow finer structures to be observed while producing increasing amounts of image data to be interpreted by radiologists. However, even the latest CADx systems often fail to incorporate clinical information, to use optimized feature extraction, or to apply machine learning techniques.

Features of interest that have not been developed include analysis for both thick and thin slice CT scans. Other proposed features include only simple 3D features or features that are not optimal to describe the differences between benign and malignant nodules. These features often result in a low rate of accuracy and are not desirable to use in a CADx algorithm.

The methods and systems provided herein are based on state-of-the art machine learning techniques, such as genetic algorithms and support vector machines, and innovative image processing algorithms for pre-processing of images and feature extraction. An aspect of the methods and systems provided herein is the capability of combining image-based and clinical information about a patient and a patient's lesion into the decision making process. The methods and systems provided herein combine features extracted from high quality medical images, for example a CT scan, with non-imaging data from patient health records through the use of machine learning and image processing methodology.

The methods and systems (exemplified by FIG. 5) provided herein for computer-aided diagnosis of lesions includes several processing units. A pre-processing unit processes images, e.g. MSCT scans, to create isotropic volumes of interest each surrounding a lesion to be diagnosed, or to segment or delineate lesions, such as pulmonary nodules. A feature extraction unit extracts two dimensional (2D), two and a half dimensional (2.5D) and three dimensional (3D) features from images to characterize lesions. These features, together with clinical information including patient history, constitute the feature pool. A clinical information processing unit accepts and transforms the clinical information to be used in the feature pool. Feature selection, a step used in the design phase of the system, is based on a genetic algorithm, and is used to select an optimal feature subset from the feature pool. A classifier or committee of classifiers are used in the feature selection process, and are built using the selected feature subset to classify a lesion as malignant or benign, or to determine the malignancy of a lesion, such as a pulmonary nodule.

In many instances, because of the complexity of the 3D shape of the nodules, the 2D slices may reveal several disconnected islands. As many of the features described below rely upon a unique delineation of border pixels, it is often desirable to operate on only a single object. The methods and systems in one embodiment use an algorithm to remove all but the largest connected object, and perform all nodule analysis on that object. In this case, analysis is performed only for 2D and 2.5D features. The methods and systems provided herein facilitate the use of 2D, 2.5D, and 3D features on a multi-slice dataset. Because of the ease of computation of 2D features, it is often desirable to utilize 2D features even when 3D data is available. This is particularly common in thick slice data (i.e. a slice thickness greater than 3 times the in-plane resolution), where 3D features may not be as robust and sufficient. In such cases, the user of the CADx system may manually identify an individual slice for analysis. The CADx system is then said to be operating in a 2D mode, in which the features extracted from this 2D slice are used in performing the classification. Similarly, only 2D features from the training dataset are used in constructing the optimum classifier when the system is operating in 2D mode. Such systems fail to capture the full range of information present in the multi-slice volume.

To overcome this, the methods and systems provided herein use a 2.5D, or pseudo-3D, mode. The same features are used as in the pure 2D mode, and these features are calculated on each slice of the MSCT image. The slice range may encompass the whole volume, or alternatively can be manually selected by the user. The feature values used in the classifier are then taken as the size-weighted average of these slice-by-slice calculations. For some features, it may be more logical to use the maximum or minimum values across slices. Alternatively, the 2D features are computed on maximum intensity projection (MIP) data taken through the range of slices, or from an arbitrary angle, with the 2D feature extraction run on the projected image.

Pre-Processing of Images

Images, such as MSCT scans, are pre-processed to determine regions of interest (ROIs) or volumes of interest (VOIs) for analysis. These serve as an input into the feature extraction unit.

The methods and systems provided herein include several pre-processing steps. ROIs are constructed that allow feature calculation to be robust to segmentation errors. ROIs are constructed by morphological operations of erosion and dilation on the binary nodule image. This is used to construct an internal, external, and boundary region. An additional ROI consisting of the largest square region that can be embedded in the object is also identified. The features described in these methods and systems can be computed using any one or more of these ROIs.

The chest wall and other irrelevant anatomy are excluded from feature calculation. Many current segmentation algorithms also delineate the borders of the chest wall. Voxels or pixels that belong to the chest wall are explicitly excluded from all of the features to be described. Only those pixels that are labelled as belonging to the lung parenchyma or the nodule of interest are included.

For many features, it is desirable to capture the full range of detail within the nodule, including potential cavities within the nodule. Cavitation, or air pockets within the nodule, is often not identified directly by segmentation. Therefore, the methods and systems provided herein use an algorithm for post-processing nodule segmentation to fill in holes or gaps in the segmentation mask, such that air pockets or cavities within the nodule are explicitly considered during feature calculation. No change is performed on the CT images, but rather, on the segmentation results. These methods and systems relate to the use of the post-processed segmentation masks, as well as the original segmentation masks.

As shown in FIG. 5, the pre-processing unit extracts a VOI surrounding a lung nodule based on its location, which can be provided by a clinician or a CAD system.

Since MSCT scans have higher resolution in the slices than among slices, it is desirable to perform interpolation between the slices to create isotropic voxel representation. Interpolation to isotropic voxels is desirable for segmentation purposes. However, it is also preferable to retain the original data for feature calculation, to avoid the filtering properties of interpolation kernels. The methods and systems provided herein use an interpolation method that keeps the original slices and inserts interpolated slices to make the scan near-isotropic. The methods and systems in one embodiment include a means of limiting the interpolation to a single axis in order to reach near-isotropic voxels. These isotropic volumes can then be used for segmentation, and for computation of 3D features. The original 2D slices can later be extracted from this interpolated 3D dataset.

A segmentation step delineates the pulmonary nodules from the background, generating a binary or trinary image (label VOI), where a nodule, background and lung wall regions are labeled. A segmentation algorithm is run on the interpolated data, resulting in a volume of the same dimension as the interpolated volume. See Philips Press Release, Philips' new CT Lung Nodule Assessment and Comparison Option can enable clinicians to identify and treat lung cancer, 2003; Wiemker et al., Options to improve the performance of the computer aided detection of lung nodules in thin-slice CT, Philips Research Laboratories: Hamburg, p. 1-19, 2003; and Wiemker et al., Computer Aided Tumor Volumetry in CT Data, Invention disclosure, Philips Research Hamburg, 2002. For analysis of 2D features, the slices in the label volume that correspond to the original slices are identified and extracted. For 3D features, the full near-isotropic 3D volume is used.

In one embodiment of the invention, manual selection of segmentation masks from segmentation using varying threshold is used. Thus, various segmentation thresholds and seed placements are tested. Grayscale images overlaid with segmentation contours are presented to a user, who then manually selects the optimum segmentation, a single slice for 2D feature extraction, and a range of slices for 2.5-D feature extraction.

Feature Extraction Unit

Feature extraction is performed to extract 2D, 2.5D, and 3D features images to characterize lesions, such as pulmonary nodules. These features, together with clinical information, constitute a feature pool.

Using a gray-level and labeled VOI, the feature extraction unit calculates different features, such as 2D (using the native slice of the VOI with the largest nodule cross-section), 2.5D (an average of 2D features calculated on all the native slices, weighted by the nodule cross-sectional area), and 3D (based on the near-isotropic VOI) features. The feature extraction step is significant, since the calculated features need to have enough discriminatory power together with the clinical information to distinguish between malignant and benign nodules. Features can be, for example, gray level distributions inside and surrounding the nodules, shape information, texture information inside and outside the nodule, gradient information on the surface of the nodule, or contrast between the inside and outside of the nodule. Each of these features can be calculated in 2D, 2.5D, or 3D.

Clinical Information and its Transformation to Clinical Features

Since clinical information is important in the diagnosis process, the methods and systems provided herein include a unit which converts clinical information into a suitable form so it can be combined with extracted image based features for the feature selection process. For example, clinical information for gender is divided into 2 categories, such as whether the patient is male or whether is the patient female. The clinical information which can be used in the proposed system can include, for example, age, gender, smoking history, cancer history, family history, occupational exposure, recreational exposure, past or present pulmonary diseases (e.g. emphysema), number of satellite nodules around the one to be diagnosed, size of lymph nodes, presence of other suspicious nodules, or location of the nodule in the lung (e.g. upper lobe or lower lobe).

Feature Selection

The feature selection unit finds the most relevant features from the feature pool containing image-based as well clinical features. A GA and SVM-based feature selection process is used. Once the most relevant features are determined based on a training dataset, a classifier or committee of classifiers is built based on the optimal feature subsets and the feature selection unit is no longer required. In the embodiment relating to the committee of classifiers, each committee member can be constructed on a feature subset identified through a separate run of the feature selection algorithm. The diversity of the classifiers in the committee is achieved for example for the GA-based feature selection by giving a different randomly selected set of training and testing data to each GA run. Other feature selection methods, such as statistical difference filters, correlation filters, stepwise linear regression, recursive feature elimination (RFE), and a random feature selection can also be used.

Classifier

Following the supervised learning principle, a classifier is built using the selected optimal feature subset and training data. Possible classifiers are SVMs, decision trees, linear discriminant analysis and neural networks. SVMs are often used since they have shown superior performance with respect to classifiers.

Committees of classifiers can also be used. In this case, several classifiers are built on different feature subsets, which were selected as the best feature subsets via the feature selection process. Each classifier will result in a decision, e.g. whether a nodule is malignant or benign. A majority vote of the classifiers will determine for example, the output of the CADx system for the nodule in question. In likelihood CADx, the output likelihood of the committee may be the fraction of positive votes, or an average (which may be weighted) of the individual likelihood results from each member of the committee.

EXAMPLES

The methods and systems provided herein apply several image processing methods to CADx. Examples of these image processing methods are provided below.

Example 1: Invariant Moments

Moments are a means of mathematically representing the spatial distribution of an object. This includes the shape (binary moments) or density distribution (grayscale moments). Invariant moments are those moments that do not change when the object undergoes some transformation, such as rotation, scaling, and translation. Moment based methods have been used at length in computer vision and optical character recognition. The use of invariant moments, including the first 6 invariant moments, is described by the mathematical formalism of Hu (1962).

For an image I of size N×M, the moments $m_{pq}$ can be given by:

$$m_{pq} = \sum_{x=1}^{N}\sum_{y=1}^{M} x^p y^q I(x, y)$$

where I takes on the grayscale intensity of the image at a pixel (x, y) for grayscale moments, or a value of 0 or 1 for binary moments. The centroid of the object is defined using the following moments.

$$\bar{x} = m_{10}/m_{00} \text{ and } \bar{y} = m_{01}/m_{00}$$

These allow calculation of centralised moments $\mu_{pq}$ that are invariant under translation:

$$\mu_{pq} = \sum_{x=1}^{N}\sum_{y=1}^{M} (x-\bar{x})^p (y-\bar{y})^q I(x, y)$$

which can be made scale invariant by computing normalised central moments $$\eta_{pq} = \mu_{pq}/\mu_{00}^{\gamma}$$

where $\gamma = (p+q)/2 + 1$ for all $(p+q) \geq 2$

These scale and translation invariant moments can be converted into rotationally invariant moments, using a method described by Hu (IRE Trans Information Theory, IT-8 179-197, 1962). These seven moment invariants are given as the following equations.

$$H_1 = \eta_{20} + \eta_{02}$$

$$H_2 = (\eta_{20} - \eta_{02})^2 + 4\eta_{11}^2$$

$$H_3 = (\eta_{30} - 3\eta_{12})^2 + (3\eta_{21} - \eta_{03})^2$$

$$H_4 = (\eta_{30} - \eta_{12})_2 + (\eta_{21} + \eta_{03})^2$$

$$H_5 = (\eta_{30} - 3\eta_{12})(\eta_{30} + \eta_{12}) + ((\eta_{30} + \eta_{12})_2 - 3(\eta_{21} - \eta_{03})^2)$$

$$H_6 = (\eta_{20} - \eta_{02})((\eta_{30} + \eta_{12})^2 - (\eta_{21} + \eta_{03})^2) + 4\eta_{11}(\eta_{30} + \eta_{12})(\eta_{21} + \eta_{03})$$

$$H_7 = (3\eta_{21} - \eta_{03})(\eta_{30} + \eta_{12})((\eta_{30}\eta_{12})^2 - 3(\eta_{21} + \eta_{03})^2) + (3\eta_{12}) - \eta_{30})(\eta_{21} + \eta_{03})(3(\eta_{12} + \eta_{30})^2 - (\eta_{21} + \eta_{03})^2)$$

The moments and central moments are computed by iterating over different p and q values and over all pixels in an image, skipping over pixels that are not in the nodule. The image function, I, can be binary or real-valued, and in practice, both are implemented. In this way, each nodule can contribute seven invariant binary moments, and seven invariant grayscale moments. These 14 scalar values can then be used as inputs into a CADx system.

Alternatively, to make the feature extraction robust to segmentation uncertainty, the grayscale moments are calculated by performing the moment calculation on a circular area enclosing the segmented nodule. The pleural wall and irrelevant lung structures are identified via the segmentation and removed. To avoid incorrectly placing 0 values in these removed structures, random noise is inserted into these pixels by sampling from a histogram computed from the retained background.

Further, 3D moments are extracted, and features are derived from the 3D moments in binary mask gray scale data as shown by the following equations.

$$\text{moment\_}J11 = \eta_{200} + \eta_{020} + \eta_{002}$$

$$\text{moment\_}J21 = \eta_{200}\eta_{020} + \eta_{200}\eta_{002} + \eta_{020}\eta_{002} - \eta_{101}^2 - \eta_{110}\eta_{110} - \eta_{011}^2$$

$$\text{moment\_}J31 = \eta_{200}\eta_{020}\eta_{002} - \eta_{002}\eta_{110}^2 + 2*\eta_{110}*\eta_{101}*\eta_{011} - \eta_{020}*\eta_{101}^2 - \eta_{200}*\eta_{011}^2$$

The three derived features above are also computed for moments derived for the grayscale nodule image.

Example 2: Invariant Fourier Descriptors

Fourier descriptors are a means of mathematically describing the shape of an object. Conceptually, the border of an object is described in terms of frequencies. Low frequencies describe smooth edges and give the general shape of the object, whereas high frequencies describe irregularities and sharp changes in the contour. The Fourier descriptors describe the particular mix of frequencies that constitute a particular object shape. In the methods and systems provided herein, Fourier descriptors that are invariant to scale, translation, and rotation are used. For use in the classifier, two means of condensing the Fourier coefficients into a scalar value are provided.

Initially, the pixels on the edge of a nodule are identified by a number of well-known methods. Care is taken to ensure that these N edge pixels are listed in clockwise or counter-clockwise order around the object. Each edge pixel is described with its x and y coordinate, yielding the vectors $x = \{x_1, x_2, \ldots, x_N\}$ and $y = \{y_1, y_2, \ldots, y_N\}$. The discrete Fourier transform for each object is computed using any of a number of techniques (denoted generically as FT), yielding $$v = FT\{x\} \text{ and } w = FT\{y\}$$

which can be decomposed into real and imaginary parts $$v_n = a_n + ib_n \text{ and } w_n = c_n + id_n.$$

The Fourier descriptors for the shape uniquely defined by x and y is then expressed as:

$$f_n = \frac{\sqrt{a_n^2 + b_n^2}}{\sqrt{a_1^2 + b_1^2}} + \frac{\sqrt{c_n^2 + d_n^2}}{\sqrt{c_1^2 + d_1^2}}.$$

This yields a vector f which may vary in length between nodules, thus rendering it difficult to use in comparing nodules in a CADx system. In the methods and systems provided herein, vector f is condensed into two scalar descriptors $g_1$ and $g_2$:

$$g_1 = \left(\sum_{n=2}^{N} \frac{f_n}{n}\right) / \sum_{n=2}^{N} n \text{ and } g_2 = \left(\sum_{n=2}^{N} nf_n\right) / \sum_{n=2}^{N} n.$$

The mathematical description given here follows that of Nixon et al., Feature Extraction & Image Processing, Butterworth-Heinemann: Woburn, Mass. pp. 269-278 (2002). This calculation is used as an input into a CADx system.

Example 3: Fractal Dimension of Nodule Shape

The contour of an object can be described using the Minkowski-Bouligand fractal dimension, also known as the box-counting dimension. This describes how the measured length of the contour changes with the resolution at which the contour is viewed. A nodule with a high fractal dimension tends to exhibit irregularities in the surface shape, which may indicate malignancy. The fractal dimension can be calculated for 2D, 2.5D, or 3D features, and in fact, all three may be simultaneously used during classification.

Figure 1:
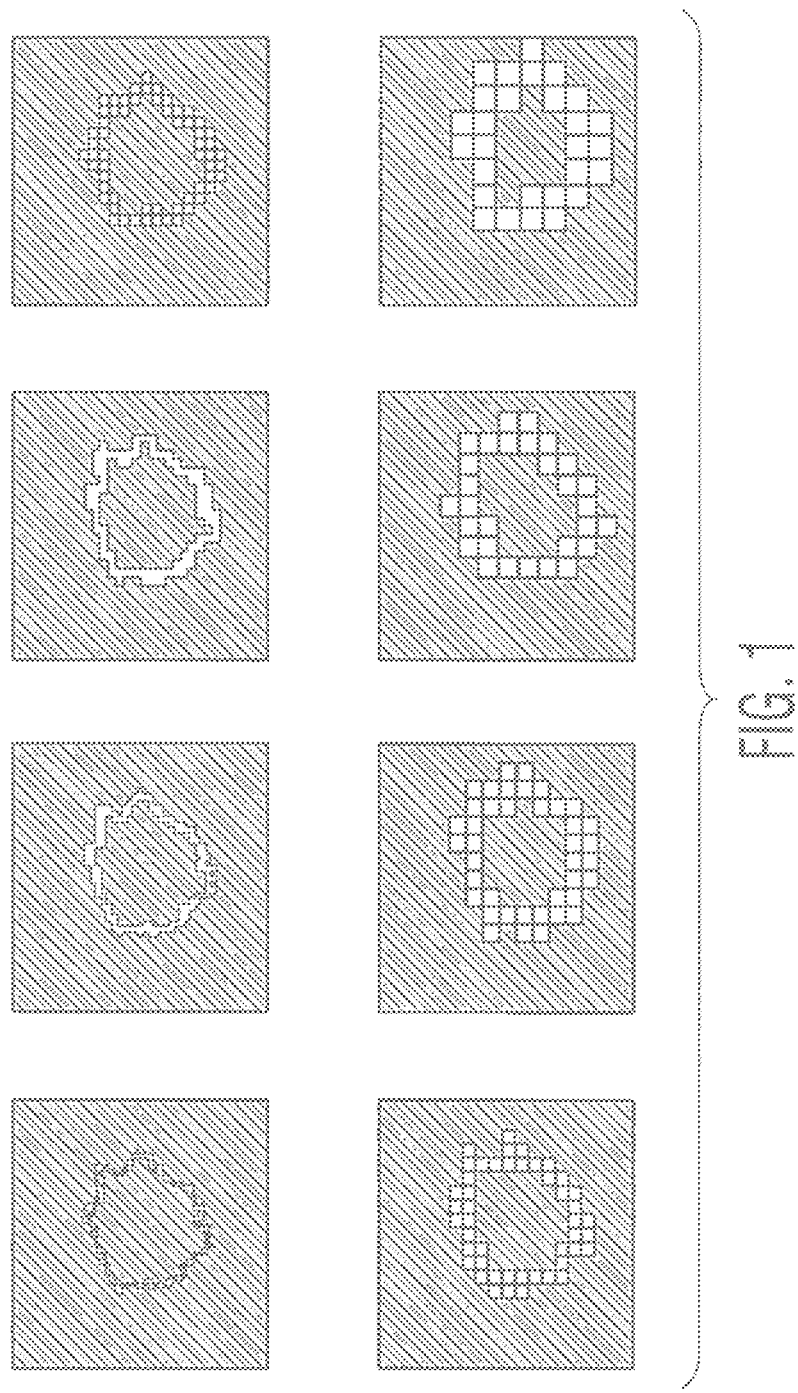
FIG. 1 is a series of drawings showing a box-counting algorithm for finding fractal dimension of a contour.

A nodule with an outline, shown in the first panel of FIG. 1 (Scale 1), is considered. This outline consists of all pixels that are nearest to the exterior of the nodule. The total number of pixels in the outline is tallied as N (1). The image is then resampled by a factor of ½, shown in FIG. 1 as Scale 2. This can be thought of as tiling 2×2 pixel boxes over the Scale 1 image and seeing how many of these boxes contain and edge pixels. This count of boxes is denoted N (½). This is then repeated with 3×3 pixel boxes to yield N (⅓), and so on. For a fractal object, the value N (1/d) varies with the scale d according to.

$$N(1/d) = \mu((1/d)^{-FD}$$

where FD is the fractal dimension of the object. By algebraic manipulations, this is changed to:

$$\ln N(1/d) = -FD \ln (1/d) + \ln \mu.$$

Figure 2:
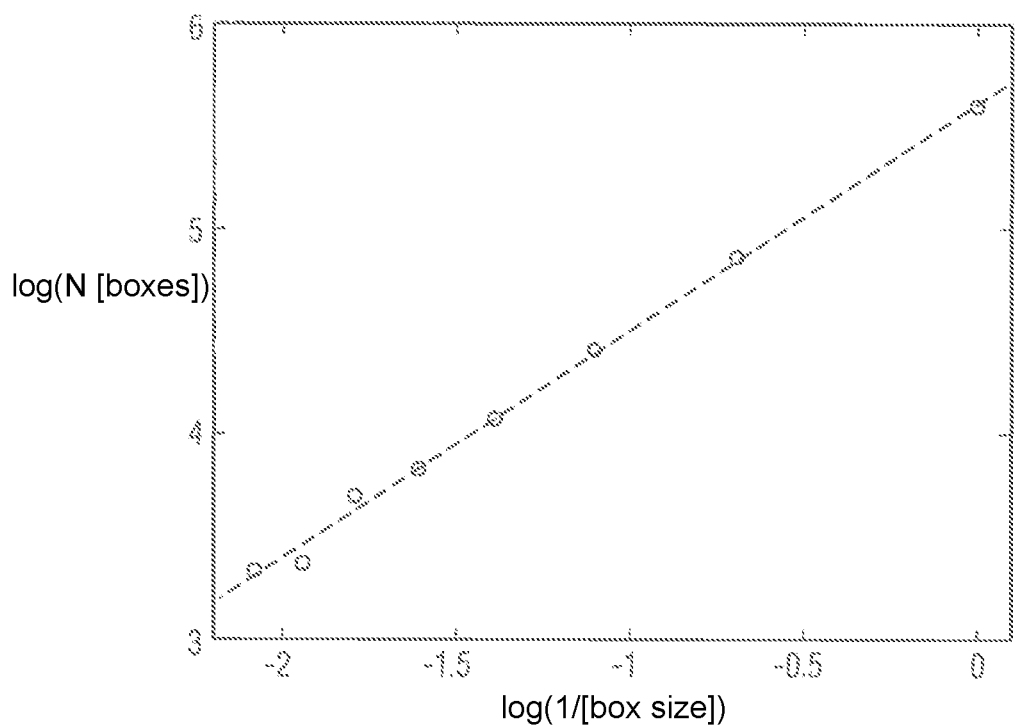
FIG. 2 is a graph of a computation of fractal dimension, with log (N [boxes]) on the ordinate and log (1/[box size]) on the abscissa, showing a linear relationship between log (N [boxes]) and log (1/[box size]).

Thus, if the value of of $N_d$ is computed for several d, then the FD can be estimated by a linear fit between ln (1/d) on the x-axis and ln N (1/d) on the y-axis. This fit may be a least squares fit or a robust fit, or may be taken by taking the average slope between successive points. An example of such a fit is given in FIG. 2. The slope of this line is used as a feature in a CADx system.

Example 4: Fractal Dimension of Nodule Texture

The texture of an object can be described in terms of fractal dimension. A 2D view of the object is considered as a surface embedded in 3D. The fractal dimension measures the variations in grayscale intensity as the resolution of the image is changed. Higher fractal dimensions suggest greater complexity in the internal structure of the object. As with the border, the fractal dimension of the texture can be calculated for 2D, 2.5D, or 3D features, and in fact, all three may be simultaneously used during classification.

The texture dimension is calculated in a manner similar to that of the border, described above in Example 3, with the following changes: the d×d boxes are not tiled, but overlap; that is, all possible d×d boxes are considered. Then, instead of counting the number of boxes, N (1/d) represents the differences between the maximum and minimum pixel gray value within each d×d box, summed over all boxes of size d×d.

Example 5: Edge Gradient-Based Features

Border pixels of a nodule are identified, and the normal direction pointing away from an object is computed. The derivative is then estimated by computing the difference in grayscale intensity between the border pixel and the pixel some finite distance away in the normal direction. This second external value is typically found by interpolating the value of the image two pixels away. The derivative as a function of position along the contour can then be analyzed statistically to yield scalar features using the mean, the standard deviation, and the root-mean-square variation and first moment of the power spectrum of this function.

As with the Fourier descriptors, each edge pixel and its x and y coordinate are considered, yielding the vectors $x=\{x_1, x_2, \ldots, x_N\}$ and $y=\{y_1, y_2, \ldots, y_N\}$. For an edge pixel i located at $(x_i, y_i)$, the normal angle is computed. This is given by:

$$\alpha = \frac{1}{2}\left(\tan^{-1}\left(\frac{y_{i+k} - y_i}{x_{i+k} - x_i}\right) + \tan^{-1}\left(\frac{y_i - y_{i-k}}{x_i - x_{i-k}}\right)\right) + 90°,$$

taking care to ensure the consistency of the signs. That is, the normal is computed as being perpendicular to the local curve of the surface, where the local curvature is estimated by averaging between two nearby (but not necessarily adjacent) points. An example of these angles as computed on a nodule is given in FIG. 3.

A point d pixels away from the edge is then defined by the coordinates $x=x_i+d \sin \alpha$ and $y=y_i+d \cos \alpha$, with an intensity at that location found by bilinear interpolation on the image. The edge gradient is then simply the difference between the interpolated intensity and the intensity of the original edge pixel. This can be computed for every edge pixel in order, as shown in FIG. 4. A large number of statistical features can be calculated from this, including mean and standard deviation. The power spectrum can estimated through many well known techniques, thus yielding information about the frequency content of the fluctuations around the object. The underlying assumption to this analysis is that high frequency variations in intensity may suggest spiculations, which are believed to be an indicator of malignancy. To assess this, the moments and root mean square variation of the power spectrum can be calculated and used as features.

Example 6: Detection and Characterization of Internal Clusters

The presence of dark or bright clusters in the object may be indicative of calcification or cavitation, respectively. The methods and systems provided herein include means of identifying these regions automatically, and using them as features for CADx.

A threshold is iteratively applied to an image, such that the only pixels that remain are above some intensity t. The value of t is lowered, starting at the maximum value in the object to the minimum value of the object. At each threshold, the remaining pixels are grouped into clusters that are connected on the sides. That is, each cluster consists of a set of pixels where it is possible to move from one pixel to any other pixel by travelling in one of the four cardinal directions, without ever leaving the cluster. If the largest cluster has a size of greater than n pixels, then the value of the threshold t is saved and the algorithm halted. The feature that is extracted is the given by either the threshold value expressed in units of image pixel intensity, or as the number of standard deviations between the mean intensity of the rest of the detected cluster and the critical threshold. Similarly, by thresholding below the iterated intensity threshold, it is possible to detect dark clusters; the same two features can be calculated for these clusters.

Example 7: Chain Code

The pixels on the border of an object image can be identified in a continuous order, such that each pixel has a pair of neighbors. By tracking the relative positions of neighboring pixels, a vector describing the shape of an object is identified.

For each pixel on the border, the two neighbors of this pixel are defined using a chain code. Turning to FIG. 6, consider a border given by pixels a-g of image 602.

By placing the centre of template 604 on each of pixel a-g of the boundary, the chain code description is read out {1, 2, 1, 2, 4, 4, . . . } with a difference between successive values of {1, −1, 1, 2, 0, . . . } or an absolute difference of {1, 1, 1, 2, 0, . . . }.

The distribution of these chain code and chain code difference values can be used to calculate features. The fraction of absolute difference values greater than 1, 2, . . . , 6 can be used as a feature. This fraction can be used to detect the number of sudden changes in direction, thus describing the irregularity of nodules, or concepts such as spiculation and lobulation.

Example 8: Texture: Neighbourhood Gray-Tone Difference Matrix

Several mathematical methods exist for approximating the human perception of texture of an image, including the aforementioned fractal method. An alternative method is based on what is known as the neighborhood gray-tone difference matrix (NGTDM). This method seeks to quantitatively describe the differences between each pixel and its surrounding neighborhood, leading to mathematical descriptions that have been shown in psychometric tests to correlate well with subjective ratings of the abstract qualities including coarseness, contrast, busyness, complexity, and strength.

The description given by Amadsun and King (IEEE Trans Sys Man Cybernetics 19(5): 1264-1274, 1989) is followed. The NGTDM is a matrix formed as follows. The N×N image as a whole is quantized to a predetermined number of levels, g. For every pixel in the particular ROI with quantized intensity denoted by f(k,l), $$A(k, l) = \frac{1}{(2d+1)^2 - 1} \left[ \sum_{m=-d}^{d} \sum_{n=-d}^{d} f(k+m, l+n) \right] \text{ where}$$

$(m, n) \neq (0, 0)$

That is, A is the average of a (2d+1)×(2d+1) neighborhood around the pixel of interest, excluding the pixel itself. The NGTDM matrix N has one column and as many rows as their are levels of intensity in the image. The row i is then given by $$N(i) = \sum_{k,l} |i - A(k, l)|$$

where the summation is taken over all pixels where f(k,l)=i Care is taken to restrict the calculation to the area within the region of interest (ROI), whether this is a nodule itself or the region outside the nodule.

The probability for each bin, p(i), is defined as the fraction of centre pixels that contributed to the calculation of N(i). Two features are shown here; others are described in detail in Amad sun et al., IEEE Trans Sys Man Cybernetics, 19(5): 1264-1274, 1989. These features are:

$$\text{coarseness} = \left[ \sum_i p(i)N(i) \right]^{-1}$$

$$\text{contrast} = \left[ \frac{1}{G(G-1)} \sum_{i=0}^{g} \sum_{j=0}^{g} p(i)p(j)(i-j)^2 \right] \left[ \frac{1}{n^2} \sum_{i=0}^{g} N(i) \right]$$

where n=(N−2d) and G is the actual number of the g levels that appear in the image.

The methods and systems provided herein include pre-processing CT images for CADx, several new features that can be used as inputs into a CADx system and advanced machine learning techniques for feature selection and classification. The methods and systems provided herein overcome difficulties in dealing with thick-slice CT volumes, provide robustness to errors in identifying the border of lung nodules, and are optimized to improve diagnostic accuracy of classification systems. The methods and systems provided herein use pre-processing and features to solve this problem by providing 2D, 2.5D, and 3D characterization of lesions, such as benign and malignant lung nodules. Therefore, a machine learning system using uses these features can distinguish more accurately benign nodules from malignant nodules and can achieve higher specificity and sensitivity than the systems without them. Furthermore, the proposed system has the capability of combining image-based and clinical information about the patient into the decision making process.

The CADx methods and systems provided herein can be used with several modalities, for example MRI and CT. The methods and systems provided herein can be used in radiology workstations (exemplified but not limited to Philips Extended Brilliance Workstation, Philips Mx8000, and Philips Brilliance CT scanners) or incorporated into PACS systems (e.g. Stentor iSite). The CADx methods and systems provided herein can be used in diagnosing different diseases, including but not limited to colon polyps, liver cancer, and breast cancer.

It will furthermore be apparent that other and further forms of the invention, and embodiments other than the specific and exemplary embodiments described above, may be devised without departing from the spirit and scope of the appended claims and their equivalents, and therefore it is intended that the scope of this invention encompasses these equivalents and that the description and claims are intended to be exemplary and should not be construed as further limiting. The contents of all references cited herein are incorporated by reference.

What is claimed is:

1. A method of extracting features from a multi-slice data set, the method comprising:
   representing a spatial distribution of an object mathematically;
   representing a shape of the object mathematically;
   determining contour and texture of the object;
   identifying a border pixel of the object and estimating a derivative;
   analyzing the derivative as a function of position along the contour;
   identifying automatically the presence of dark regions or bright regions within the object; and
   approximating texture of an image in a surrounding region of the object;
   wherein the features are calculated for the group comprising each slice of the multi-slice data set, a maximum intensity projection taken at an arbitrary angle, a minimum intensity projection taken at an arbitrary angle, and a digitally reconstructed radiograph taken at an arbitrary angle through one or more slices of the image.

2. The method according to claim 1, further comprising selecting an individual slice from the multi-slice data set for analysis by a manual selection by a user or by an automatic selection of a largest slice.

3. The method according to claim 1, wherein the features calculated for each slice of the multi-slice data set are combined by a method selected from the group consisting of:
   calculating a weighted average in which weights are proportional to a number of pixels on each slice;
   finding a maximum value across multiple slices of the multi-slice data set; and
   finding a minimum value across the multiple slices of the multi-slice data set.

4. The method according to claim 1, wherein the features are calculated in each of a plurality of dimensions.

5. The method according to claim 4, wherein the plurality of dimensions is at least one selected from the group consisting of 2 dimensions, 2.5 dimensions, and 3 dimension.

6. The method according to claim 1, wherein the shape of the object is described by at least one of the group consisting of:
   distribution of coefficients after a Fourier transform of border pixel positions;
   mathematical moments of a segmented object that are invariant to translation, rotation, and scaling;
   mathematical moments of a grayscale distribution of image pixels;

fractal dimension; and a chain code.

7. The method according to claim 1, wherein the texture of the object is described by at least one of the group consisting of:

fractal dimension;

energy, entropy, maximum probability, inertia, inverse difference and correlation based on a gray-level co-occurrence matrix; and coarseness, contrast, busyness, complexity and strength based on a neighborhood gray-tone difference matrix.

8. The method according to claim 1, wherein the surrounding region is described by at least one of the group consisting of:

a derivative of image intensity along a direction orthogonal to a local contour;

a derivative of the image intensity along the direction orthogonal to the local contour and moments of a power spectrum; and an estimate of variance of the image intensity along the direction orthogonal to the local contour.

9. The method according to claim 1, wherein the presence of dark regions and bright regions within the object is described by the intensity or size of clusters of contiguous pixels above or below a given threshold.

10. A system for extracting features from a multi-slice data set, the system comprising:

a processor; and a memory storing instructions, which, when executed by the processor, cause the processor to:

represent a spatial distribution of an object mathematically; 0067 represent a shape of the object mathematically;

determine contour and texture of the object; identify a border pixel of the object and estimate a derivative;

analyze the derivative as a function of position along the contour; identify automatically the presence of dark regions or bright regions within the object; and approximate texture of an image in a surrounding region of the object;

wherein the features are calculated for the group comprising each slice of the multi-slice data set, a maximum intensity projection taken at an arbitrary angle, a minimum intensity projection taken at an arbitrary angle; and a digitally reconstructed radiograph taken at an arbitrary angle through one or more slices of the image.

11. The system according to claim 10, wherein the memory further stores instructions, which, when executed by the processor, cause the processor to select an individual slice from the multi-slice data set for analysis by a manual selection by a user or by an automatic selection of a largest slice.

12. The system according to claim 10, wherein the features calculated for each slice of the multi-slice data set are combined by one of the group consisting of:

calculating a weighted average in which weights are proportional to a number of pixels on each slice;

finding a maximum value across multiple slices of the multi-slice data set; and finding a minimum value across the multiple slices of the multi-slice data set.

13. The system according to claim 10, wherein the features are calculated in each of a plurality of dimensions.

14. The system according to claim 13, wherein the plurality of dimensions is at least one selected from the group consisting of 2 dimensions, 2.5 dimensions, and 3 dimension.

15. The system according to claim 10, wherein the shape of the object is described by at least one of the group consisting of:

distribution of coefficients after a Fourier transform of border pixel positions;

mathematical moments of a segmented object that are invariant to translation, rotation, and scaling;

mathematical moments of a grayscale distribution of image pixels;

fractal dimension; and a chain code.

16. The system according to claim 10, wherein the texture of the object is described by at least one of the group consisting of:

fractal dimension;

energy, entropy, maximum probability, inertia, inverse difference and correlation based on a gray-level co-occurrence matrix; and coarseness, contrast, busyness, complexity and strength based on a neighborhood gray-tone difference matrix.

17. The system according to claim 10, wherein the surrounding region is described by at least one of the group consisting of:

a derivative of image intensity along a direction orthogonal to a local contour;

a derivative of the image intensity along the direction orthogonal to the local contour and moments of a power spectrum; and an estimate of variance of the image intensity along the direction orthogonal to the local contour.

18. The system according to claim 10, wherein the presence of dark regions and bright regions within the object is described by the intensity or size of clusters of contiguous pixels above or below a given threshold.

* * * * *